United States Patent [19]

Margetts et al.

[11] 4,361,703

[45] Nov. 30, 1982

[54] PARA-AMINO(OR NITRO)PHENYL N-ACETYLAMINOTHIOALKANOATES

[75] Inventors: George Margetts, Billingshurst; Roderic S. Andrews, Newcastle-upon-Tyne, both of England; Jean Legros, Dijon, France

[73] Assignee: Sterling Drug Inc., New York, N.Y.

[21] Appl. No.: 246,234

[22] Filed: Mar. 23, 1981

Related U.S. Application Data

[62] Division of Ser. No. 26,329, Apr. 2, 1979, which is a division of Ser. No. 909,846, May 26, 1978, Pat. No. 4,181,719.

[30] Foreign Application Priority Data

May 26, 1977 [GB] United Kingdom ............... 22218/77

[51] Int. Cl.$^3$ ........................................... C07C 69/773
[52] U.S. Cl. .................................. 560/142; 560/146; 562/556
[58] Field of Search ............................... 560/142, 146

[56] References Cited

U.S. PATENT DOCUMENTS 3,591,686 7/1971 Sheffner .
3,996,268 12/1976 Carpenter et al. .................. 560/142
4,038,306 7/1977 Milkowski et al. ................. 560/142

FOREIGN PATENT DOCUMENTS 4672M 12/1966 France .

OTHER PUBLICATIONS

*Lancet*, Apr. 20, 1974, p. 729.
*Lancet*, Sep. 27, 1975, pp. 610-611.
*Lancet*, Oct. 2, 1976, pp. 738-739.
*Lancet*, Mar. 19, 1977, pp. 657-658.
*Biochem. Pharmacology*, vol. 24, pp. 37-42, 1975.
Derwent B: Pharmaceuticals, W22-25/5/75, p. 6.
Kovach; Dissertation Abstracts International B, 1975 36 (2), pp. 734-735.
Yeung et al., J. Biol. Chem., vol. 254 (1979), pp. 9453-9457.
McOmie, J. F. W., *Protective Groups in Organic Chemistry*, Plenum Press, N.Y. 1973, pp. 46, 58 and 59.

*Primary Examiner*—Johnnie R. Brown
*Assistant Examiner*—Frederick W. Pepper
*Attorney, Agent, or Firm*—Robert K. Bair; B. Woodrow Wyatt

[57] ABSTRACT

N-acetyl-para-aminophenyl N'acetylaminothioalkanoates I are new analgesic compounds with greatly reduced hepatotoxic effects, when taken in overdose, relative to N-acetyl-para-aminophenol. They are prepared by reacting an N-acetylaminothioalkanoic acid IV with a reactive organic chloride V to form a mixed anhydride II and then reacting the latter with N-acetyl-para-aminophenol. The mixed anhydrides II are new and useful intermediates. Alternatively the derivatives I may be prepared by reacting the acid IV with bis-(4-nitrophenyl) sulfite to form a para-nitrophenyl N-acetylaminothioalkanoic acid ester VIII, reducing the latter to a para-aminophenyl-N-acetylaminothioalkanoate VII, and acetylating this product. The esters VII and VIII are new and useful intermediates. Both reactions may pass through S-blocked intermediates, which are also new. Pharmaceutical compositions containing the derivatives I are disclosed, and also analgesic methods using them.

2 Claims, No Drawings

PARA-AMINO(OR NITRO)PHENYL N-ACETYLAMINOTHIOALKANOATES

CROSS-REFERENCE TO RELATED APPLICATIONS

This application is a division of copending Application Ser. No. 26,329, filed Apr. 2, 1979, in turn, a division of Application Ser. No. 909,846, filed May 26, 1978 and now U.S. Pat. No. 4,181,719, issued Jan. 1, 1980.

BACKGROUND OF THE INVENTION (a) Field of the Invention

This invention is concerned with analgesic compounds, processes for making them and the compounds thus prepared, various intermediates useful in their synthesis, and pharmaceutical compositions incorporating these analgesic compounds. More especially, the invention relates to N-acetyl-para-aminophenyl N'-acetylaminothioalkanoates which are useful as analgesic agents having analgesic activity like that of N-acetyl-para-aminophenol but being largely free from the hepatotoxic effects normally encountered when N-acetyl-para-aminophenol is taken in overdose.

(b) Description of the Prior Art

The compound N-acetyl-para-aminophenol, also known as acetaminophen, paracetamol, para-hydroxyacetanilide, APAP, NAPA, etc., is a widely used analgesic agent. Unfortunately the toxic nature of the drug when taken in overdose has been given wide publicity; and coupled with its ready availability this had led to the increasing use of this drug in suicide. The major organ affected by an overdose of N-acetyl-para-aminophenol is the liver; and even when an overdose is not fatal, it can cause severe liver damage.

Although this invention is not limited by any theoretical considerations, the following background explanation is offered. It is thought that hepatic damage induced by N-acetyl-para-aminophenol is related to the metabolism of the drug converting it into a highly chemically-reactive derivative, which binds covalently to liver cell proteins when the drug is given in overdose; whereas non-hepatotoxic doses of N-acetyl-para-aminophenol give rise to little or no convalent binding. Although the exact nature of the toxic metabolite is not known, it is thought to be a precursor of the cysteine and mercapturic acid conjugates of N-acetyl-para-aminophenol, as excretion of these conjugates increases significantly in the overdose situation.

The cysteine and mercapturic acid conjugates of N-acetyl-para-aminophenol are formed via the activation of the parent molecule to a chemically-unstable intermediate, which normally will immediately form a complex with reduced glutathione within the liver cell. In the overdose situation, however, activation of N-acetyl-para-aminophenol occurs faster than hepatic reduced glutathione can be synthesized; and as the level of glutathione falls, some of the reactive metabolite combines with hepatocyte proteins instead. The quantity of the chemically-unstable intermediate convalently bound to hepatocyte proteins correlates with the severity of the ensuing liver damage.

In the overdose situation, the logical antidote would therefore seem to be glutathione itself; but, if administered exogenously, glutathione fails to penetrate the cells, and is therefore ineffective unless massive doses are administered. Instead therefore it is conventional to treat overdoses with glutathione substitutes—sulfhydryl compounds—e.g., cysteamine or dimercaprol. It has been suggested that cysteamine may inhibit oxidation of N-acetyl-para-aminophenol to the toxic metabolite.

There is also a less obvious way of tackling the same problem. While an N-acetyl-para-aminophenol overdose results in glutathione depletion, it should be remembered that glutathione synthesis is still taking place—so by providing a glutathione precursor it should be possible to promote glutathione synthesis, thus to reduce the rate at which the glutathione levels fall, and in this way to keep the glutathione levels from falling to the low level at which the active N-acetyl-para-aminophenol metabolite starts to attack the hepatocyte proteins. Here again therefore it is conventional to treat overdoses of N-acetyl-para-aminophenol by providing a glutathione precursor, e.g. methionine or cysteine.

These conventional methods of treating overdoses of N-acetyl-para-aminophenol are however often ineffective, due to the time lapse between ingestion of the N-acetyl-para-aminophenol overdose and the arrival of the glutathione substitute or glutathione precursor in the liver cells.

The following references are summarized to show the state of the prior art:

A. E. M. McLean, THE LANCET, p. 729 (Apr. 20, 1974), first showed the combination of methionine with paracetamol as a way of greatly reducing the lethal and hepatotoxic effects of paracetamol overdosage. McLean concludes: "Methionine seems an easy way in which we can make paracetamol a safer drug" and also suggests the use of cystine as a substitute for methionine.

Maxwell et al., THE LANCET, pp. 610–611 (Sept. 27, 1975), reported that the above-noted McLean's study "demonstrated the decreased toxicity of the combination of acetaminophen and methionine in rats" and that "our study demonstrates it in dogs".

McLean and Day, "The Effect of Diet on the Toxicity of Paracetamol and the Safety of Paracetamol-Methionine Mixtures", Biochemical Pharmacology 24, 37–42 (1975)—The abstract reads in part: "Addition of methionine to oral paracetamol dose protects against death and liver injury, and it is suggested that this may be a useful technique for making paracetamol safe against the danger of overdose."

The National Research Development Corp. German Pat. Appln. No. 2,455,203, published May 22, 1975, (based on Appln. No. 455,203, filed Nov. 21, 1974, in turn, based on British Appln. No. 54,098, filed Nov. 21, 1973) is abstracted in the July 8, 1975 DERWENT® GERMAN PATENTS GAZETTE as follows:

"Medicaments contg. p-hydroxyacetanilide (I) as active ingredient also contain a cpd. (II) which is a precursor of the central amino acid grouping of glutathione and which can be converted into glutathione in vivo. (I) is widely used as an analgesic and antipyretic, but overdoses give rise to liver necrosis associated with the absence of glutathione in the liver; if an overdose of (I)+(II) is taken, this automatically leads to an increase in the glutathione synthesised in the organism, thus counteracting the toxic effects of the overdose. The glutathione precursor (II) can be an S-contg. amino acid, pref. DL- or L-cysteine, -cystine or -methionine (esp. the L-form), or a di- or tripeptide contg. such an amino acid. The medicament pref. contains 10–50% (esp. 10–30%) of (II), based on the wt. of (I). The medicaments are pref. administered orally (esp. as elixirs or tablets) in a unit dose of 0.25–1 g."

The Italchemi S.r.l.-Instituto Chimico Farmaceutico French BSM No. 4672M, published Jan. 23, 1967, shows as anti-inflammatory, anti-allergic, analgesic and antipyretic agents the paracetamol esters of gamma-aminobutyric acid, delta-aminovaleric acid and epsilon-aminocaproic acid and their N-acetyl derivatives.

Kovach, "Aminoacid esters of p-acetamidophenol as prodrugs", a Ph.D. thesis, University of Kansas, 1974 [C.A. 83, 193681t (1975); Diss. Abstr. Int. B 1975, 36(2), 734–5]—The abstract of this thesis shows the preparation of paracetamol (APAP) esters of amino acids, specifically glycine, alpha-aspartic acid and beta-aspartic acid.

Piperno et al. (McNeil Labs. Inc., Fort Washington, Pa.), THE LANCET, pp. 738–739 (Oct. 2, 1976)—Letter to the editor with the title, "Reversal of Experimental Paracetamol Toxicosis with N-Acetylcysteine". The authors conclude that their data "suggest that N.A.C. sodium (N-acetylcysteine sodium) will be effective orally and parenterally in the clinic at doses approximately to 20–40% of the ingested amount of paracetamol".

Gerber et al. (Dept. of Pharmacology, Vanderbilt University, School of Medicine, Nashville, Tenn.), THE LANCET, pp. 657–658 (Mar. 19, 1977)—Letter to the editor with heading: "Effect of N-Acetylcysteine on Hepatic Convalent Biding or Paracetamol (Acetaminophen)". Gerber et al. reported that 1 g./kg. of N-acetylcysteine administered concurrently or 2 or 4 hours after 1.4 g./kg. of paracetamol "significantly improved 48 hour survival in mice".

Mead Johnson & Co. Sheffner U.S. Pat. No. 3,591,686, issued July 6, 1971 (based on Appln. Ser. No. 657,498, filed Aug. 1, 1967, in turn a C.I.P. of Appln. Ser. No. 482,931, filed Aug. 26, 1965) has "method-of-treating" and composition claims covering the use of N-acetylcysteine and related"—(N-acylamino)-$\beta$-mercaptoalkanoic acids or salts thereof" as anti-inflammatory agents.

SUMMARY OF THE INVENTION

The present invention is based partly upon the premise that by chemically combining a glutathione precursor with N-acetyl-para-aminophenol it ought to be possible to minimize the danger of liver damage in the overdose situation—for the act of ingesting an overdose of N-acetyl-para-aminophenol should then ipso facto ensure that the sulfhydryl groups needed in a glutathione precursor will simultaneously be present in the liver to help replenish the glutathione stores.

Important though it is, that is not the only advantage of the present invention. We have also found that the chemical combination of N-acetyl-para-aminophenol with a glutathione precursor possesses an extremely palatable flavor, far more acceptable than the extremely bitter taste of the former, and is moreover free from the pronounced odor of the latter.

According to one aspect of this invention there are therefore provided, as new compounds of analgesic activity but relatively free from related hepatotoxic effects when taken in overdose, the N-acetyl-para-aminophenyl N'-acetylaminothioalkanoates which conform to the general formula I

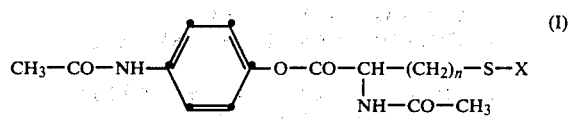

in which n is 1 or 2; and X is a hydrogen atom, a methyl group or a grouping of general formula I'

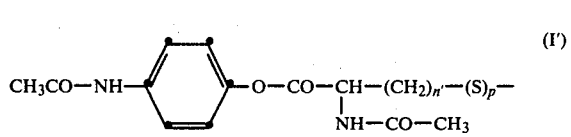

wherein n' is 1 or 2; and p is zero or 1.

Specific preferred N-acetyl-para-aminophenyl N'-acetylaminothioalkanoates of general formula I above, for use in accordance with this invention, are for instance as follows:

N-Acetyl-para-aminophenyl N'-acetyl-methionate of the structural formula:

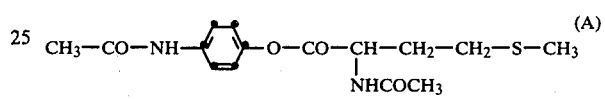

(conforming to general formula I above, where n is 2 and X is a methyl group);

N-Acetyl-para-aminophenyl N'-acetyl-cysteinate of the structural formula:

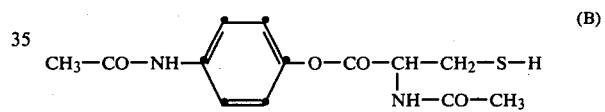

(conforming to general formula I above, where n is 1 and X is a hydrogen atom);

Di-(N-acetyl-para-aminophenyl) N',N''-diacetyl-cystinate of structural formula:

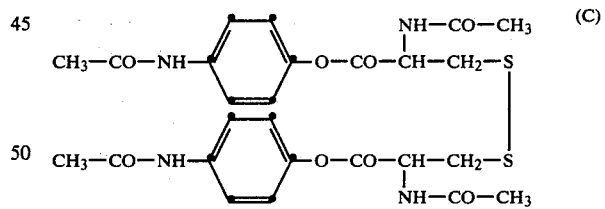

(conforming to general formula I above, where n is 1 and X is the grouping of general formula I' where p is 1 and n' is 1);

Di-(N-acetyl-para-aminophenyl) N',N''-diacetylcystathionate of structural formula:

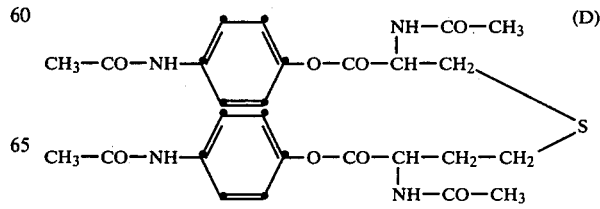

(conforming to general formula I above, where n is 1 and X is the grouping of general formula I' wherein p is 0 and n' is 2);

N-Acetyl-para-aminophenyl N'-acetyl-S-methylcysteinate of the structural formula:

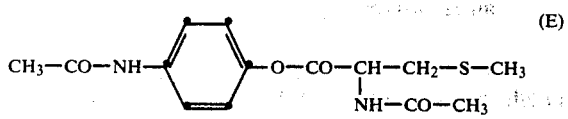
(E)

(conforming to general formula I above, where n is 1 and X is a methyl group); and N-Acetyl-para-aminophenyl N'-acetyl-homocysteinate of the structural formula:

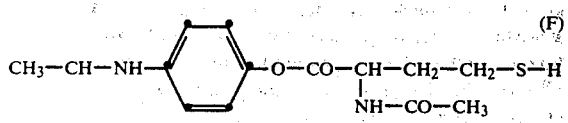
(F)

(conforming to general formula I above, where n is 2 and X is a hydrogen atom).

All the N-acetyl-para-aminophenyl N'-acetylaminothioalkanoates of general formula I above, and specifically the preferred ones of structural formula A–F above, include at least one asymmetric carbon atom, and therefore exist as separate optically-active D and L isomers, as well as in the form of mixtures of the D and L isomers, above all as the equiproportioned racemic mixture in which the compounds will normally be prepared unless optically-active starting materials are employed in the processes described below. This invention of course extends to all the compounds of formula I as individual optically-active D and L isomers and also in the form of mixtures thereof, especially as racemic mixtures. Because it is the L-amino acids which occur naturally in the body, we prefer when economic considerations permit to use the L-isomers of the compounds of this invention, thus for instance N-acetyl-para-aminophenyl N'-acetyl-L-cysteine and N-acetyl-para-aminophenyl N'-acetyl-L-methionate.

We have moreover found that these N-acetyl-para-aminophenyl N'-acetylaminothioalkanoates of general formula I above, and specifically the preferred ones of structural formulae A–F above, can be conveniently prepared, usually in good yield, by various alternative procedures.

According to another aspect of this invention there is therefore provided a process for preparing the N-acetyl-para-aminophenyl N'-acetylaminothioalkanoates of general formula I above, which includes the step of reacting a mixed anhydride of general formula II

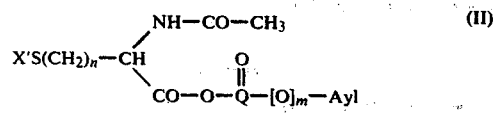
(II)

wherein n is 1 or 2; m is zero or 1; Q represents either a carbon atom C or when m is zero a sulfinyl group S=O; "Ayl" represents an alkyl group with 1–20 carbon atoms, an aryl group with 6–20 carbon atoms, an alkaryl group with 7–20 carbon atoms or an aralkyl group with 7–20 carbon atoms; and X; is a hydrogen atom, a blocking group, a methyl group, or a mixed anhydride group conforming to the general formula II'

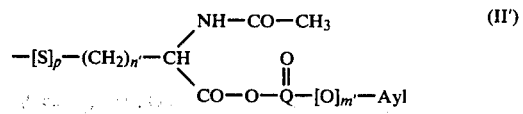
(II')

in which Q and Ayl both have their previously-indicated meanings; n' is 1 or 2'; m' is zero or 1; and p is zero or 1, with N-acetyl-para-aminophenol to form the corresponding N-acetyl-para-aminophenyl N'-acetylaminothioalkanoate, and thereafter when X' is a blocking group this is removed, thus yielding the desired corresponding N-acetyl-para-aminophenyl N'-acetylaminothioalkanoate of general formula I.

The reaction between the mixed anhydride II and N-acetyl-para-aminophenol can and preferably should be performed in an anhydrous inert organic solvent. For reasons which will appear below it should be noted that this reaction can moreover be conducted without detriment in the presence of a base, such as a tertiary amine like triethylamine or pyridine.

The invention extends to the N-acetyl-para-aminophenyl N'-acetyl-aminothioalkanoates formed in the course of the above-described reaction wherein X' is a blocking group, thus those which conform to the general formula III

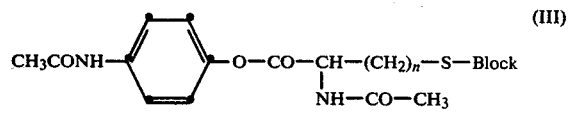
(III)

in which n is 1 or 2; and "Block" represents a blocking group or a mixed anhydride group conforming to the general formula III'

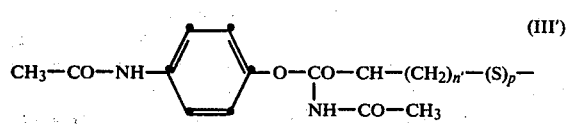
(III')

in which n' is 1 or 2; and p is zero or 1, which are new intermediates useful in synthesis.

The mixed anhydrides of general formula II used as starting material in the above-described reaction may advantageously be prepared in a preliminary stage by reacting an N'-acetylaminothioalkanoic acid or blocked derivative thereof of general formula IV

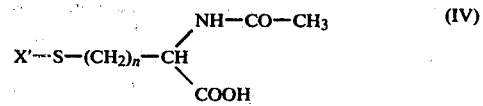
(IV)

in which n is 1 or 2; and X' is a hydrogen atom, a blocking group, a methyl group or a grouping of general formula IV'

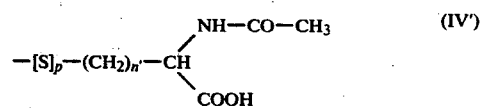
(IV')

wherein n' is 1 or 2' and p is zero or 1, or a salt thereof with a reactive organic chloride of general formula

in which "Ayl" represents an alkyl group with 1-20 carbon atoms, an aryl group with 6-20 carbon atoms, an alkaryl group with 7-20 carbon atoms or an aralkyl group with 7-20 carbon atoms; m is zero or 1; and Q represents either a carbon atom C or when m is zero a sulfinyl group S=O, in the presence of a base to yield the desired corresponding mixed anhydride of general formula II.

The reactive organic chloride of general formula V above can for instance be an alkyl, aralkyl, aryl or alkaryl chloroformate of general formula Va

or a sterically-encumbered alkyl, aralkyl, aryl or alkaryl acid chloride of general formula Vb

or an alkyl, aralkyl, aryl or alkaryl sulfonyl chloride of general formula Vc

in all of which general formulae Va, Vb and Vc "Ayl" represents an alkyl, aralkyl, aryl or alkaryl group having up to 20 carbon atoms therein.

The reaction (sometimes hereinafter called the "first-stage reaction") between the aminothioalkanoic acid (or blocked derivative thereof) of general formula IV or a salt thereof and the reactive chloride of general formula V (or Va, Vb or Vc) is most conveniently carried out in an anhydrous inert and usually organic solvent, preferably a polar organic solvent, for example, either a substituted aromatic solvent such as toluene or any halogenated aromatic hydrocarbon, or most desirably a halogenated aliphatic hydrocarbon such as dichloromethane or above all chloroform (trichloromethane).

This first-stage reaction must be performed in the presence of a base, which advantageously will be a tertiary amine, and preferably either triethylamine or pyridine.

As previously indicated, the subsequent reaction between the mixed anhydride and N-acetyl-para-aminophenol sometimes hereinafter called the "second-stage reaction") is advantageously performed in the same anhydrous inert organic solvent as that in which the first-stage reaction is performed, and the second-stage reaction moreover suffers no detriment from the presence of base. It is therefore possible and indeed desirable to carry out both the first-stage reaction and the second-stage reaction in the same anhydrous inert organic solvent, without intervening isolation of the first-stage reaction product, and usually in the same reaction vessel.

This invention extends to the blocked N'-acetylaminothioalkanoic acid derivatives IV which may be used as starting material in the first-stage reaction just described, thus those which conform to the general formula VI

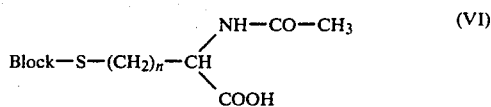

in which n is 1 or 2; and "Block" represents a blocking group which are new intermediates useful in synthesis.

In cases where it is desired to prepare an N-acetyl-para-aminophenyl N'-acetylaminothioalkanoate of general formula I wherein X is a hydrogen atom, it may often be advisable, and sometimes indeed may be necessary, to employ a blocked N'-acetylaminothioalkanoic acid derivative VI as starting material in the first-stage reaction, so as to protect the S—H bond from attack during that and the subsequent second-stage reaction. This can be effected in a manner well known and understood in the art, by substituting the hydrogen of the S—H bond with a blocking group, for instance, tetrahydro-2-pyranyl, from dihydropyran.

In the preparation of an N-acetyl-para-aminophenyl N'-acetylaminothioalkanoate of general formula I wherein X is a hydrogen atom, the overall process should therefore desirably include the initial step of preparing the blocked N'-acetylaminothioalkanoic acid derivative VI for use therein by substituting the S—H bond of an N'-acetylaminothioalkanoic acid of general formula IV wherein X is hydrogen with a blocking group before the first-stage reaction with the reactive organic chloride V, and also include the final step of replacing the blocking group in the corresponding N-acetyl-para-aminophenyl N'-acetylaminothioalkanoate with a hydrogen atom after the reaction with N-acetyl-para-aminophenol.

The blocking group used is preferably one derived from dihydropyran, that is, tetrahydro-2-pyranyl.

According to a still further aspect of this invention there is also provided an alternative process for preparing the N-acetyl-para-aminophenyl N'-acetylaminothioalkanoates of general formula I, which includes the step of reacting a para-aminophenyl N-acetylaminothioalkanoate of general formula VII

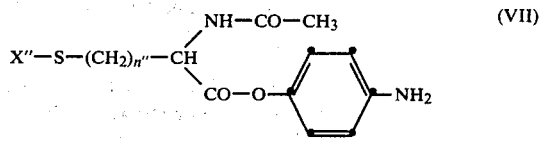

in which n" is 1 or 2' and X" is a hydrogen atom, a blocking group, a methyl group or a grouping of the general formula VII'

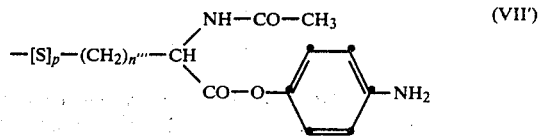

wherein n''' is 1 or 2; and p is zero or 1, with an acetylating agent to yield the corresponding N-acetyl-para-aminophenyl N'-acetylaminothioalkanoate, and thereafter when X" is a blocking group this is removed, thus yielding the desired corresponding N-acetyl-para-aminophenyl N'-acetylaminothioalkanoate of general formula I.

The acetylation of the para-aminophenyl N-acetylaminothioalkanoate VII can be performed using any convenient acetylating agent, such as preferably acetic anhydride.

The invention extends to the para-aminophenyl N-acetylaminothioalkanoates VII used as starting material in the reaction just described, which are new intermediates useful in synthesis.

These para-aminophenyl N-acetylaminothioalkanoates VII can be prepared in a preliminary stage of the process described immediately above by reacting a para-nitrophenyl N'-acetylaminothioalkanoate of general formula VIII

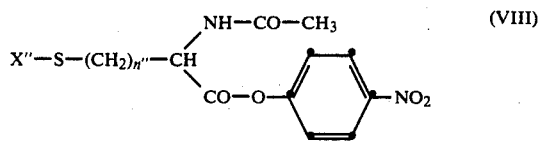

in which n" is 1 or 2; and X" is a hydrogen atom, a blocking group, a methyl group or an ester grouping conforming to the general formula VIII'

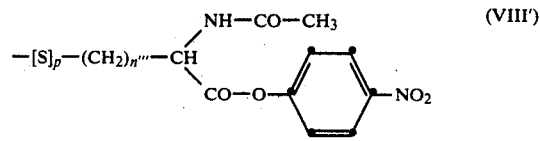

wherein n''' is 1 or 2; and p is zero or 1, with a reducing agent.

The reduction of the para-nitrophenyl N-acetylaminothioalkanoate VIII can best be carried out using nascent hydrogen as the reducing agent, which can most conveniently be by iron powder and acid, preferably hot acetic acid.

The invention extends to the para-nitrophenyl N'-acetylaminothioalkanoates VIII used as starting materials in the preliminary stage of the process just described, which are new intermediates useful in synthesis.

These para-nitrophenyl N'-acetylaminothioalkanoates VIII can in turn be prepared in an initial stage of this alternative process by reacting an N-acetylaminothioalkanoic acid of general formula IV with bis-(4-nitrophenyl) sulfite.

The reaction between the N-acetylaminothioalkanoic acid IV and the bis-(4-nitrophenyl) sulfite is advantageously carried out in solution in a tertiary amine, preferably pyridine; and it can and conveniently should be carried out at ambient or near-ambient temperature.

As with the other, first-described process, in cases where it is desired to prepare an N-acetyl-para-aminophenyl N'-acetylaminothioalkanoate of general formula I where X is a hydrogen atom, it may often be advisable, and sometimes indeed it may be necessary, to employ a blocked N'-acetylaminothioalkanoic acid, thus one of general formula VI, as the starting material above, so as to protect the S—H bond from attach during the subsequent reaction stages. As before, this can be effected in a manner well known and understood in the art, by substituting the hydrogen of the S—H bond with a blocking group, for instance, tetrahydropyranyl.

In the preparation of an N-acetyl-para-aminophenyl N'-acetylaminothioalkanoate of general formula I wherein X is a hydrogen atom, this alternative process overall should therefore desirably include the initial step of preparing the blocked derivative of N-acetylaminothioalkanoic acid of general formula VI for use therein by substituting the S—H bond of an N'-acetylaminothioalkanoic acid ester derivative of general formula IV wherein X is hydrogen with a blocking group before reaction with the bis-(4-nitrophenyl) sulfite, and also include the final step of replacing the blocking group in the corresponding N-acetyl-para-aminophenyl N'-acetylaminothioalkanoate with a hydrogen atom after the reaction with the acetylating agent.

As already indicated above, the blocking group used will preferably be tetrahydro-2-pyranyl, which is derived from dihydropyran. Of course, other blocking groups capable of blocking or protecting thiols can be used provided the blocked thiol, e.g., thioether, thioacetal, thiolester, etc., can be readily reconverted to the thiol.

Preferred groups for "Ayl", as used herein, e.g., in the definition of the compounds of formula II, include: methyl, ethyl, n-propyl, isopropyl, n-butyl, 2-butyl and isobutyl when "alkyl"; phenyl, 2-chlorophenyl, 3-chlorophenyl and 4-chlorophenyl when "aryl"; benzyl when "aralkyl"; and, ortho-tolyl, meta-tolyl and para-tolyl when "alkaryl".

For employment in human medicine as an analgesic the N-acetyl-para-aminophenyl N'-acetylaminothioalkanoates of this invention should, of course, be suitable formulated into pharmaceutical compositions by association with suitable pharmaceutical vehicles.

The term "pharmaceutical" is used herein to exclude any possibility that the nature of the vehicle (considered, of course, in relation to the route by which the composition is intended to be administered) could be harmful, rather than beneficial. The choice of a suitable vehicle for any chosen route and mode of presentation is believed to be within the competence of those accustomed to the preparation of pharmaceutical compositions.

Accordingly, in yet another aspect of this invention, there are provided pharmaceutical compositions containing one or more of the N-acetyl-para-aminophenyl N'-acetylaminothioalkanoates of general formula I above in association with a suitable pharmaceutical vehicle as herein defined.

The compositions of this invention may be administered orally or rectally. In respect of these various modes of presentation the "pharmaceutical vehicle" is preferably:

(a) the ingestible excipient of a tablet, coated tablet, or pill; the ingestible container of a capsule or cachet; the ingestible pulverulent solid carrier of a powder; or the ingestible liquid medium of a syrup, solution, suspension or elixir; or (b) a base material of low melting point capable of releasing the active ingredient to perform its pharmacological function, which base material, when appropriately shaped, forms a suppository.

While the modes of presentation just listed represent those most likely to be employed, they do not necessarily exhaust the possibilities.

The N-acetyl-para-aminophenyl N'-acetylaminothioalkanoates of this invention will most frequently be administered in the form of tablets, capsules and other solid unit-dose forms. Bearing in mind the dosage rates recommended below it will frequently be desirable to employ the composition in the form of solid unit-doses containing substantially 500 mg. of the N-acetyl-para-aminophenyl N'-acetylaminothioalkanoic acid ester derivatives.

While the dosage rates for the analgesic N-acetyl-para-aminophenyl N'-acetylaminothioalkanoates of general formula I above will, to a certain degree, depend upon the route by which the compositions are to be administered, and of course also upon the condition to be treated, it can as a general indication be said that the useful dose normally will be within the range of from 1 g. to 4 g. of the active analgesic per day for an adult.

It may conveniently here be noted that the N-acetyl-para-aminophenyl N'-acetylaminothioalkanoates of general formula I above can of course be administered in medicine and where appropriate be formulated into pharmaceutical compositions for that purpose, in conjunction with other pharmacologically-active ingredients, such as for instance one or more of the following, namely N-acetyl-para-aminophenol, codeine, codeine phosphate, caffeine, caffeine hydrate, caffeine citrate, butobarbitone, famprofazone, propyphenazone, chlormezanone, phenolphthalein, aspirin, acetomenaphthone, orphenadrine citrate, phenobarbitone, dihydrocodeine tartrate, dextropropoxyphene and pseudoephedrine hydrochloride. Of course, it will be realized that the relative freedom from hepatotoxic effects enjoyed by the N-acetyl-para-aminophenyl N'-acetylaminothioalkanoates of general formula I above will not extend to any such overdoses of the other ingredients.

In order that the invention may be well understood, it will now be described in more detail, though by way of illustration only, with reference to the following examples:

GROUP I—PREPARATIONS OF DERIVATIVES OF GENERAL FORMULA I VIA THE MIXED ANHYDRIDES OF GENERAL FORMULA II

EXAMPLE 1

Preparation of N-acetyl-para-aminophenyl N'-acetyl-D,L-methionate (A) via the mixed anhydride.

Stage A: Preparation of the Mixed Anhydride (II, where n=2 and X'=Me)

To a mixture of 19.1 g of N-acetylmethionine and 9.45 of methyl chloroformate in 200 ml of chloroform 21 g of triethylamine were added dropwise, while maintaining the temperature below 15° C. When addition was complete the mixture was refluxed for 15 minutes then allowed to cool to room temperature.

Stage B: Conversion of the Mixed Anhydride into the Methionate (A)

15.1 g of N-acetyl-para-aminophenol were added to the reaction product from Stage A and the mixture was refluxed for 1.5 hours. The mixture was allowed to cool to room temperature, 100 ml of water were added and the mixture was shaken vigorously until precipitation of the product occurred.

The product was collected and dried in vacuum, to yield 13 g of N-acetyl-para-aminophenyl N'-acetyl-D,L-methionate, m. pt.=183° C.

EXAMPLE 2

Preparation of N-acetyl-para-aminophenyl N'-acetyl-S-methylcysteinate (E) via the mixed anhydride Stage A: Preparation of the Mixed Anhydride (II, where n=1 and X'=Me)

To a mixture of 17.7 g of N-acetyl-S-methylcysteine and 9.45 g of methyl chloroformate in 200 ml of chloroform 21 g of triethylamine was added dropwise, while maintaining the temperature below 15° C. When addition was complete the mixture was refluxed for 15 minutes, then allowed to cool to room temperature.

Stage B: Conversion of the Mixed Anhydride into the Cysteinate (E)

15.1 g of N-acetyl-para-aminophenol were added to the reaction product obtained from Stage A, and the mixture was refluxed for 1.5 hours. The mixture was then allowed to cool to room temperature, and 100 ml. of water were added, and the mixture shaken vigorously until precipitation of the product occurred.

The product was collected and dried in vacuum, to yield N-acetyl-para-aminophenyl N'-acetyl-S-methylcysteinate.

EXAMPLE 3

Preparation of di-(N-acetyl-para-aminophenyl) N',N''-diacetylcystinate (C) via the mixed anhydride Stage A: Preparation of the Mixed Anhydride (II, where n=1, X'=II', p=1 and n'=1

21.7 g (0.2 mole) of ethyl chloroformate in 100 ml of chloroform were added to a mixture of 32.4 g (0.1 mole) of N,N'-diacetylcystine and 20.2 g (0.2 mole) of triethylamine in 250 ml of chloroform, over a period of half to one hour, keeping the temperature at 20° C. Immediately after the addition of the ethyl chloroformate was completed, a further 4.04 g (0.04 mole) of triethylamine were added.

Stage B: Conversion of the Mixed Anhydride into the Cystinate (C)

The temperature of the reaction product obtained from Stage A was adjusted to 20°–25° C., and 30.2 g (0.2 mole) of N-acetyl-para-aminophenol were added portionwise. This mixture was stirred at 25° C. for three hours. The product recovered by filtration was the desired di-(N-acetyl-para-aminophenyl) N',N''-diacetylcystinate.

EXAMPLE 4

Preparation of N-acetyl-para-aminophenyl N'-acetylcysteinate (B) via the mixed anhydride, with preliminary blocking and subsequent deblocking of the S—H bond Preliminary Stage X: Complete Blocking of Starting Material A mixture of 32.6 g of N-acetyl-L-cysteine, 18.0 g of dihydropyran and a trace of conc. hydrochloric acid was refluxed in 150 ml. of dichloromethane for 40 minutes.

The solution was filtered and concentrated under reduced pressure, to yield 50 g of the desired tetrahydropyran derivative as a colorless oil.

Preliminary Stage Y: Partial Deblocking of Starting Material

A solution of 40 g of the tetrahydropyran derivative, obtained from Preliminary Stage X above, dissolved in 55 ml of methanol, was added while stirring to 250 ml. of 1 M aqueous sodium hydroxide solution, and the stirred mixture was kept at room temperature for 25 minutes.

The mixture was then extracted with ethyl acetate (to remove unreacted tetrahydropyran derivative) and the aqueous layer was neutralized with a solution of 15.2 g of acetic acid in 50 ml. of water. The aqueous solution was re-extracted with ethyl acetate (2×100 ml), and the ethyl acetate extracts were combined and dried over magnesium sulfate. The ethyl acetate solution was concentrated under reduced pressure, and after stripping off residual solvents under high vacuum 7.8 g of the desired S-tetrahydropyranyl-N-acetylcysteine were obtained as an oil.

Stage A: Preparation of the blocked Mixed Anhydride (II, where n=1, m=1, Q=C, Ayl=Et and X'=tetrahydropyranyl A stirred mixture of 7.2 g of the S-tetrahydropyranyl-N-acetyl-L-cysteine obtained above and 3.2 g of ethyl chloroformate in 75 ml of toluene was cooled to 10° C. and 3.2 g of triethylamine were slowly added at such a rate as to keep the temperature in the range of 10°–15° C.

Stage B: Conversion of the Mixed Anhydride into the blocked Cysteinate (III, where n=1)

The reaction mixture was allowed to warm up to room temperature, and then a solution of 4.4 g of N-acetyl-para-aminophenol and 1.45 g of sodium hydroxide in 30 ml of water was added. The mixture was stirred vigorously for 15 minutes, then the aqueous and toluene layers were decanted from the residual oil. The oil was dissolved in 50 ml of ethyl acetate, washed with 10% aqueous sodium carbonate solution (2×100 ml), and dried over magnesium sulfate. Concentration of the ethyl acetate solution under reduced pressure gave an oil, which crystallised from chloroformether (1:2) at 0° C. overnight, yielding 1.5 g of the desired N-acetyl-para-aminophenyl N'-acetyl-S-tetrahydropyranyl-L-cysteinate, m. pt.=170°–172° C.

Subsequent Stage Z: Deblocking to form the Cysteinate (B)

A solution of 0.5 g of N-acetyl-para-aminophenyl N'-acetyl-S-tetrahydropyran-L-cysteinate in 80 ml of chloroform was stirred vigorously with 1 M hydrochloric acid for 6 hours. The chloroform layer was then removed, dried over magnesium sulfate and concentrated under reduced pressure to an oil. Trituration of the oil with ether yielded 0.32 g of the desired N-acetyl-para-aminophenyl N'-acetyl-L-cysteinate, as a white solid, m. pt.=135°–138° C.

GROUP II Preparation of Derivatives of General Formula I via the para-nitrophenyl-substituted Intermediates of General Formula VIII

EXAMPLE 5

Preparation of N-acetyl-para-aminophenyl N'-acetyl-D,L-methionate

Stage A: Preparation of para-nitrophenyl N-acetyl-D,L-methionate

A solution of 16.8 g of N-acetyl-D,L-methionate in 50 ml of pyridine was added to a solution of 28.5 g of bis(4-nitrophenyl) sulfite in 90 ml. of pyridine; and the dark mixture was kept at room temperature for 1 hour. Concentration of the dark mixture under reduced pressure at a temperature below 40° C. gave a dark oil, which was dissolved in 100 ml of ethyl acetate and washed first with 2 M hydrochloric acid then with sodium carbonate solution and finally with water, and then dried over magnesium sulfate.

After removal of the ethyl acetate under reduced pressure 100 ml of ether were added to the residual oil. This afforded cream needles, which were removed and washed with ether and suction dried. Yield 17.2 g.

Stage B: Preparation of para-aminophenyl N-acetyl-D,L-methionate

A solution of 5 g of 4-nitrophenyl N-acetyl-D,L-methionate in 80 ml of acetic acid was added slowly to a stirred mixture of 40 g of iron powder and 180 ml of hot acetic acid heated on a steam bath. After 1 hour the mixture was filtered, and the acetic acid solution was concentrated under reduced pressure to leave said product a brown gum.

Stage C: Preparation of N-acetyl-para-aminophenyl N'-acetyl-D,L-methionate

The gum was treated with 20 ml of acetic anhydride and kept for 15 minutes. 100 ml of water were added and the mixture was extracted twice with ethyl acetate. The ethyl acetate solution was concentrated under reduced pressure and the residue was treated with 50 ml of ether and allowed to stand. This gave a coating of white solid around the flask and an oil at the bottom of the flask.

The solid (2 g) was removed and recrystallised twice from ethyl acetate/methanol, m. pt.=181° C.

It is contemplated that di-(N-acetyl-para-aminophenyl) N'-acetylcystinate (C), the di-(N-acetyl-para-aminophenyl) N',N''-diacetyl-cystathionate (D) or the N-acetyl-para-aminophenol N'-acetyl-S-methyl-cysteinate (E) each will be prepared in a manner similar to that described in Example 5 above, using molar equivalent quantities of the appropriate reactants in each instance.

In Examples 1, 2, 3 and 5 above both the starting material and the final product were racemic mixtures of the D and L isomers; but it is contemplated that by using the optically-active L-isomer as starting material in each instance, the corresponding L-isomer of the final product will be obtained.

So as to show another aspect of this invention details of the formulation of N-acetyl-para-aminophenyl N'-acetyl-D,L-methionate into pharmaceutical compositions will now be given, though again only for purpose of illustration, as follows:

FORMULATION 1

Composition in the form of Tablets containing both N-acetyl-para-aminophenol and N-acetyl-para-aminophenyl N'-acetyl-D,L-methionate A tabletting mixture was made up by intimately mixing together the following ingredients:

| | |
|---|---:|
| N—Acetyl-para-aminophenol | 600.00 g |
| N—Acetyl-para-aminophenyl N—acetyl-D,L-methionate | 800.00 g |
| Maize starch | 131.48 g |
| Potassium sorbate | 1.16 g |
| Talc | 27.80 g |
| Stearic acid | 5.56 g |
| | 1566.00 g |

The mixture was then compressed by conventional tabletting machinery to form 780 mg tablets, each containing 300 mg of N-acetyl-para-aminophenol and 400 mg of N-acetyl-para-aminophenyl N'-acetyl-D,L-methionate.

FORMULATION 2

Composition in the form of Tablets containing both N-acetyl-para-aminophenol and N-acetyl-para-aminophenyl N'-acetyl-D,L-methionate in combination with other active compounds A tabletting mixture was made up by intimately mixing together the following ingredients:

| | |
|---|---|
| N—Acetyl-para-aminophenol | 540.00 g |
| N—Acetyl-para-aminophenyl N'—acetyl-D,L-methionate | 720.00 g |
| 2-(para-Chlorophenyl)-tetrahydro-3-methyl-4H-1,3-thiazin-4-one-1,1-dioxide | 200.00 g |
| Gelatin | 12.60 g |
| Maize starch | 64.00 g |
| Alginic acid | 16.20 g |
| Talc | 42.00 g |
| Stearic acid | 24.60 g |
| Magnesium stearate | 4.60 g |
| | 1624.00 g |

The mixture was then compressed by conventional tabletting machinery to form 812 mg tablets, each containing 270 mg of N-acetyl-para-aminophenol, 360 mg of N-acetyl-para-aminophenyl N'-acetyl-D,L-methionate, and 100 mg of 2-(para-chlorophenyl)-tetrahydro-3-methyl-4H-1,3-thiazin-4-one-1,1-dioxide.

FORMULATION 3

Composition in the form of Tablets

A tabletting mixture was made up by intimately mixing together the following ingredients:

| | |
|---|---|
| First granulation | |
| N—Acetyl-para-aminophenol | 240.00 g |
| N—Acetyl-para-aminophenyl N'—acetyl-D,L-methionate | 320.00 g |
| Codeine phosphate | 6.40 g |
| Sodium dioctyl sulfosuccinate 60% w/w solution | 1.312 g |
| Sorbitol | 8.40 g |
| Maize starch | 32.00 g |
| Polyethylene glycols (av. mol. wt. 6000–7500) | 9.60 g |
| Second granulation | |
| Weight of granules from first granulation | 612.702 g |
| Talc | 36.71 g |
| Magnesium stearate | 4.05 g |
| Maize starch | 4.32 g |
| Sorbitol | 96.44 g |
| Finely divided silicon dioxide (200 m²/g-BET) | 2.89 g |

The mixture was then compressed by conventional tabletting machinery to form 757 mg tablets, each containing 300 mg of N-acetyl-para-aminophenol, 400 mg of N-acetyl-para-aminophenyl N'-acetyl-D,L-methionate, and 8 mg. of codeine phosphate.

FORMULATION 4

Composition in the form of Soluble Tablets

A tabletting mixture was made up by intimately mixing together the following ingredients:

| | |
|---|---|
| N—Acetyl-para-aminophenol | 300.00 g |
| N—Acetyl-para-aminophenyl N'—acetyl-D,L-methionate | 400.00 g |
| Codein phosphate | 8.00 g |
| Caffeine | 30.00 g |
| Sorbitol | 50.00 g |
| Sodium saccharin | 10.00 g |
| Sodium bicarbonate | 1500.00 g |
| Glutamic acid | 0.90 g |
| Sodium lauryl sulfate | 0.10 g |
| Anhydrous citric acid | 925.00 g |
| Sodium carbonate | 30.00 g |
| Magnesium stearate | 0.60 g |

The mixture was then compressed by conventional tabletting machinery to form soluble 3,254 mg tablets each containing 300 mg of N-acetyl-para-aminophenol, 400 mg of N-acetyl-para-aminophenyl N'-acetyl-D,L-methionate, 8 mg of codeine phosphate and 30 mg of caffeine.

FORMULATION 5

Composition in the form of Liquid Draught

The following ingredients were mixed together:

| | |
|---|---|
| N—Acetyl-para-aminophenol | 64.8 kg |
| N—Acetyl-para-aminophenyl N'—acetyl-D,L-methionate | 106.4 kg |
| Ethyl alcohol | 383.0 kg |
| Propylene glycol | 466.0 kg |
| Glycerol | 1700.0 kg |
| Passion fruit flavour | 45.0 kg |
| Eurocol Tartrazine | 0.675 kg |
| Purified water q.s. to | 4500.00 liters | to give a mixture containing 72 mg. of N-acetyl-para-aminophenol and 118 mg of N-acetyl-para-aminophenyl N'-acetyl-D,L-methionate per 5 ml. of solution.

In all of Formulations 1–5 above it is possible of course to vary the amount of N-acetyl-para-aminophenyl N'-acetyl-D,L-methionate employed, with corresponding adjustment in the amounts of other ingredients—and some or even all of the N-acetyl-para-aminophenyl N'-acetyl-D,L-methionate can moreover be replaced by other N-acetyl-para-aminophenyl N'-acetylaminothioalkanoate of general formula I, specifically the preferred ones of structural formulae B, C, D, E and F hereinbefore identified, again if desired with appropriate adjustment of the amounts of those compounds and the other ingredients.

Finally, as illustrative, certain evaluations will be given below which indicate the freedom from undesirable side-effects and the excellent analgesic properties of one of the compounds of this invention, namely N-acetyl-para-aminophenyl N'-acetyl-D,L-methionate, of structural formula A given hereinabove, which therefore will for convenience be referred to below as "Compound A".

EVALUATION OF STABILITY

In order first to evaluate the stability of Compound A in the gastro-intestinal tract, simulated gastric and intestinal fluids and other test fluids were prepared as follows:

PREPARATION OF SIMULATED GASTRIC FLUID 0.35 gram of sodium chloride, 0.5 gram of glycine and 94 ml of M hydrochloric acid were mixed, and the volume was then made up to 1000 ml with distilled water. The pH of this system was about 1.79.

PREPARATION OF SIMULATED INTESTINAL FLUID 6.1 grams of monobasic potassium phosphate and 3.9 grams of disodium hydrogen phosphate were dissolved in 1000 ml. of water. The pH of the resulting solution was 6.85.

PREPARATION OF TRIS BUFFER 0.05 M tris buffer was made by dissolving 6.05 grams of tris-(hydroxymethyl)-methylamine in 1000 ml. of water, and adjusting the pH to 7.2 by the addition of 0.1 M HCl.

PREPARATION OF SERUM

The serum used in the assays was prepared by taking whole blood into plain tubes, incubating for one hour at 37° C., and then centrifuging at 2000 RPM for 10 minutes.

METHODS OF EVALUATION

Standard solutions of $1 \times 10^{-4}$ M Compound A in analytical grade methanol (0.01 ml) were prepared, and tested in the simulated gastric and intestinal fluids, in tris buffer alone, in tris buffer with added hog liver esterase and also in serum. The solutions under test were incorporated in 1 ml. of each of the test fluids. A temperature of 30° C. was used for the assays involving the hog liver esterase, whereas a temperature of 37° C. was used for the assays involving the simulated gastric and intestinal fluids and the serum. After this, the mixture was allowed to stand and the supernatant liquid was spotted onto silica t.l.c. plates and developed in 90:10 chloroform/methanol. The mixture was then extracted with 5 mls of chloroform and the chloroform-containing mixture was filtered through phase-separating papers, which allow only the chloroform solution to pass through. The chloroform solution was also spotted onto silica t.l.c. plates and developed in 90:10 chloroform/methanol.

RESULTS OF STABILITY EVALUATION

The results of this procedure, carried out with all the test fluids mentioned above, show that:

1. at 30° C. the presence of hog liver esterase had no effect on the rate of hydrolysis of Compound A. A half-life of about 475 minutes was recorded for Compound A in the tris buffer and also in the tris buffer plus the hog liver esterase;

2. at 37° C. the presence of human serum increased the rate of hydrolysis of Compound A. Using serum from two volunteers, half-lives of 140 and 150 minutes were recorded. The ability of human serum to hydrolyse N-acetyl-para-aminophenyl N'-acetyl-D,L-methionate indicates the presence of some specific catalytic factor which is absent from hog liver esterase. Hydrolysis of the ester in tris buffer at 37° C. gave a half-life of 240 minutes. This shows quite an increase in the rate of spontaneous hydrolysis over a 7° C. rise in temperature; and 3. the hydrolysis of the ester in simulated gastric and intestinal juice was very slow. Half-lives of 40 hours and 31.5 hours respectively were recorded.

EVALUATION OF PHARMACOLOGICAL EFFECTS

In order to demonstrate and investigate the metabolism and resultant blood-levels of N-acetyl-para-aminophenol following administration of Compound A in vivo, as compared with those obtained by administration of comparable amounts of N-acetyl-para-aminophenol itself, with or without admixture of methionine, the following experiments were performed.

(A)—Investigation of Serum Concentrations in Mice

36 Charles River COBS mice (18 males and 18 females) weighing 30 g each were deprived of food for 16 hours before the trial but were given their usual drinking water. Three groups, each containing 6 males and 6 females, received a dosage of 1 ml/100 g body weight per mouse, orally by stomach tube, of a suspension in 1% gum tragacanth of respectively:

Group X: 500 mg/kg of N-acetyl-para-aminophenol
Group Y: 500 mg/kg of N-acetyl-para-aminophenol + 500 mg/kg of methionine
Group Z: 1073 mg/kg of Compound A.

A blood sample was taken by throat-slitting from one male and one female from each Group at each study time, i.e. ½, 1, 2, 4 and 24 hours after the oral administration.

At times ½, 1, 2 and 4 hours, each serum sample was divided into three 0.1 ml trial samples for the following three determinations:

DETERMINATION 1

This determination was carried out after acidic hydrolysis, according to an adaptation of the method of Heirwegh and Fevery [*Clin. Chem.*, (1967), 13, (3), 215–219] enabling a determination to be carried out on the small trial sample. This method records N-acetyl-para-aminophenol (abbreviated as "NAPA") in any form, thus as free NAPA, conjugated NAPA and NAPA chemically-bound in Compound A or any metabolites, and the results set out below in Table I thus record "total NAPA" as measured by this method.

TABLE I

| Serum "total NAPA" (µg/ml) in Charles River Mice | | | | | |
|---|---|---|---|---|---|
| Time in hours after oral administration | | ½ hr. | 1 hr. | 2 hrs. | 4 hrs. |
| 500 mg/kg of NAPA | Male | 217 | 263 | 250 | 107 |
|  | Female | 336 | 262 | 147 | 374 |
|  | Mean | 277 | 263 | 199 | 241 |
| 500 mg/kg of NAPA + 500 mg/kg Methionine | Male | 278 | 236 | 110 | 43 |
|  | Female | 402 | 128 | 70 | 36 |
|  | Mean | 340 | 182 | 90 | 40 |
| 1073 mg/kg Compound A | Male | 96 | 255 | 67 | 94 |
|  | Female | 110 | 131 | 70 | 44 |
|  | Mean | 103 | 193 | 69 | 69 |

The results of Table I show that a significantly lower peak blood NAPA level (at ½ hour after administration) is achieved with Compound A, i.e., N-acetyl-para-aminophenyl N'-acetylmethionate or the ester of N-acetyl-para-aminophenol (NAPA) and N-acetylmethionine, than that obtained with either NAPA alone or NAPA in combination with methionine.

DETERMINATION 2

This determination was carried out by direct extraction, with no prior hydrolysis, according to an adaptation of the above-mentioned method. This method thus records "free NAPA", and the results are set out in Table II below.

TABLE II

Serum "free NAPA" (µg/ml) in Charles River Mice

| Time in hours after oral administration | | ½ hr. | 1 hr. | 2 hrs. | 4 hrs. |
|---|---|---|---|---|---|
| 500 mg/kg of NAPA | Male | 127 | 168 | 115 | 32 |
| | Female | 254 | 161 | 78 | 31 |
| | Mean | 191 | 165 | 97 | 32 |
| 500 mg/kg of NAPA + | Male | 215 | 102 | 44 | MQC |
| 500 mg/kg of Methionine | Female | 254 | 30 | MQC | MQC |
| | Mean | 235 | 66 | ~22 | |
| 1073 mg/kg of Compound A | Male | 67 | 78 | MQC | MQC |
| | Female | 66 | 74 | MQC | MQC |
| | Mean | 67 | 76 | | |

[In Table II above, MQC = Value below the minimum quantifiable concentration estimated at 20 µg/ml.]

As shown in Table I, the results of Table II also show that a significantly lower peak blood NAPA level (at ½ hr. after administration) is achieved with Compound A than that obtained with either NAPA alone or NAPA in combination with methionine.

DETERMINATION 3

This determination was carried out after 16 hours of incubation in the presence of β-glucuronidase and arylsulfatase of a Helix Pomatia juice, and direct extraction of the liberated NAPA. Colorimetry was then carried out according to the method quoted above. This method thus records what is here designated "enzymatic NAPA", including free NAPA and NAPA mainly conjugated to the glucuronides, and the results are set out in Table III below.

TABLE II

Serum "enzyme NAPA" (µg/ml) in Charles River Mice

| Time in hours after oral administration | | ½ hr. | 1 hr. | 2 hrs. | 4 hrs. |
|---|---|---|---|---|---|
| 500 mg/kg of NAPA | Male | 221 | 254 | 241 | 106 |
| | Female | 392 | 254 | 146 | 368 |
| | Mean | 307 | 254 | 196 | 237 |
| 500 mg/kg of NAPA + | Male | 294 | 192 | 97 | 50 |
| 500 mg/kg of Methione | Female | 392 | 135 | 64 | 42 |
| | Mean | 343 | 164 | 81 | 46 |
| 1073 mg/kg of Compound A | Male | 101 | 246 | 67 | 98 |
| | Female | 115 | 115 | 83 | 50 |
| | Mean | 108 | 181 | 75 | 74 |

RESULTS

The results are given in Tables I to III above and can be interpreted as follows:

NAPA administered on its own gives a high "total" or "enzymatic" serum NAPA concentration from the first ½ hour onwards after oral administration. This concentration slowly decreases but remains high up to 4 hours after oral administration.

NAPA administered in admixture with methionine gives the same high serum "total" or "enzymatic" NAPA from the first half-hour onwards, but this concentration decreases more rapidly than when NAPA is administered on its own, showing that methionine accelerates the elimination of NAPA. Compound A does not however give the acute peak observed at one-half an hour after the administration of NAPA+methionine, although the concentration of serum "total" or "enzymatic" NAPA equals that provided by the NAPA+methionine admixture one hour after oral administration, and thereafter the concentration of serum "total" or "enzymatic" NAPA then decrease according to the same kinetics as those observed with the NAPA+methionine mixture. The results of the respective "total NAPA" and "enzymatic NAPA" determinations are virtually the same for each of the samples tested, which means that NAPA is found in mouse serum, for each of the substances tested, mainly in the form of free NAPA and NAPA conjugated to the glucuronides. From all this it can be concluded that Compound A given serum NAPA concentrations in mice identical to those obtained with an equimolecular mixture of NAPA and methionine, except at one half an hour after the oral administration of the substances, when the acute peak observed is significantly lower with Compound A than that observed with the NAPA+methionine mixture, suggesting significantly less danger of overdose liver damage at this stage with Compound A than with the NAPA-methionine mixture.

(B)—Investigation of Serum Concentrations in Beagle Dogs

6 Beagle dogs (3 males and 3 females) were dosed once a day (at 08.00 hrs. each day) for 23 days with Compound A, suspended in 1% gum tragacanth, which was administered orally by oesophageal tube, at a rate of either 432 mg/kg (2 dogs, 1 male and 1 female) or 675 mg/kg (4 dogs, 2 male and 2 female). During this period the dogs received their usual food and water until 16.00 hrs. on the day before the test; but from that time until 08.00 hrs. on the day of the test they were given no food, although they received their usual drinking water. The usual dosage of Compound A was however given to the animal at 08.00 hrs. on the day of the test.

Without any further feeding, serum samples were then taken from each animal 2, 4 and 6 hours after the oral administration of Compound A, thus at 10.00 hrs., 12.00 hrs. and 14.00 hrs. on the day of the test. After the 6-hour serum sample had been taken, the animals received their usual food for a while; but they were again made to fast for 12 hours from 20.00 hrs. on the day of the test until 08.00 hrs. on the following day, when the last, 24-hour serum sample was taken.

Each sample was divided, and the NAPA in each sample-portion was determined in accordance with an adaptation of the method of Heirwegh and Fevery [*Clin. Chem.*, (1967), 13, (3), 215-219] which enables determination to be carried out on study samples of 0.1 to 0.5 ml serum.

DETERMINATION 4

A direct determination similar to that used in Determination 2 above gave results for "free NAPA" as set out in Table IV below:

TABLE IV

Serum "total NAPA" (µg/ml) in beagle dogs treated for 23 days with Compound A

| Time in hours after oral administration of the last dose of Compound A | | 2 hrs. | 4 hrs. | 6 hrs. | 24 hrs. |
|---|---|---|---|---|---|
| 432 mg/kg of Compound A | Male | 104 | 84.8 | 73.2 | 11.8 |
| | Female | 104 | 115 | 110 | 30.2 |
| | Mean | 104 | 100 | 92 | 21.0 |
| 675 mg/kg of Compound A | Male | 46.4 | 135 | 150 | 30.2 |
| | Male | 113 | 170 | 179 | 34.8 |
| | Female | 76.8 | 135 | 106 | 22.8 |
| | Female | 113 | 159 | 150 | 45.0 |

TABLE IV-continued

Serum "total NAPA" (μg/ml) in beagle dogs treated for 23 days with Compound A

Time in hours after oral administration of the last dose of Compound A

|  | 2 hrs. | 4 hrs. | 6 hrs. | 24 hrs. |
|---|---|---|---|---|
| Mean | 87 | 150 | 146 | 33.2 |

DETERMINATION 5

A determination similar to that in Determination 1 above, carried out after acid hydrolysis, gave results for "total NAPA", comprising free NAPA, conjugated NAPA and NAPA related chemically to Compound A or any metabolites, which are set out in Table V below

TABLE V

Serum "free NAPA" (μg/ml) in beagle dogs treated for 23 days with Compound A

Time in hours after oral administration of the last dose of Compound A

| | | 2 hrs. | 4 hrs. | 6 hrs. | 24 hrs. |
|---|---|---|---|---|---|
| 432 mg/kg of | Male | 30.6 | 13.8 | 7.8 | MQC |
| Compound A | Female | 37.6 | 26.0 | 11.0 | MQC |
|  | Mean | 34.1 | 19.9 | 9.4 |  |
| 675 mg/kg of | Male | 11.4 | 14.6 | 12.6 | MQC |
| Compound A | Male | 37.6 | 36.2 | 15.3 | MQC |
|  | Female | 24.6 | 12.8 | 8.2 | MQC |
|  | Female | 37.6 | 22.6 | 8.2 | MQC |
|  | Mean | 27.8 | 21.6 | 11.1 |  |

[In Table V above, MQC = value less than the minimum quantifiable concentration which is estimated to be 4 μg/ml]

The results in Table V above demonstrate that Compound A is easily hydrolyzed in this method.

From the results set out in Tables IV and V above, it will be seen that NAPA is recovered in the serum in easily determinable amounts up to 6 hours after the last oral administration of Compound A, in the two forms "free NAPA" and "total NAPA", and up to 24 hours in the single form "total NAPA".

(C)—Investigation of Analgesic Activity in Rats

In accordance with the conventional Randal-Selitto technique, groups of 12 female Charles River rats, 160–170 g in bodyweight, were injected subcutaneously in one hind-paw with yeast, and 2½ hours later, while the inflammation was ongoing, either N-acetyl-para-amino-phenol [NAPA] or N-acetyl-para-aminophenyl N'-acetyl-D,L-methionate [Compound A] was then administered orally, at a rate of either 1 or 2 millimoles/kg. A control group received only the gum tragacanth vehicle.

In order to evaluate the effect of the treatment upon pain-thresholds, pressure was applied both to the injected hind-paw and to the other non-injected hind-paw. The pain-threshold was noted as the pressure at which the rat flinched, measured using an Ugo Basile "Analgesimeter" for both hind-paws of each rat at intervals of 1 hour, 3 hours, 5 hours and 22 hours after the administration, and expressed as the percentage of the pain-threshold pressure for the injected (and thus inflamed) hind-paw as against the non-injected (and thus healthy) hind-paw.

The results (after statistical treatment by the t-test versus the control groups) are summarized in Table VI below:

TABLE VI

Percentage Pain-Thresholds in the Randall-Selitto Test in Rats

| Compound Administered | Amount in Millimoles | Amount in mg/kg | Time from Administration of Compound Tested (Time from Injection of Yeast) | | | |
|---|---|---|---|---|---|---|
| | | | 1 hr. (3.5 hrs.) | 3 hrs. (5.5 hrs.) | 5 hrs. (7.5 hrs.) | 22 hrs. (24.5 hrs.) |
| Control | — | — | 41 ± 3.1 | 42 ± 2.9 | 44 ± 4.1 | 42 ± 3.5 |
| NAPA | 1 | 151 | 45 ± 3.5 | 48 ± 4.1 | 47 ± 1.7 | 43 ± 3.4 |
| 'A' | 1 | 324 | 44 ± 3.8 | 41 ± 2.9 | 50 ±4.2 | 50 ± 2.4 |
| NAPA | 2 | 302 | 50 ±4.2 | 54 ± 4.0 P < 0.05 | 53 ±3.9 | 54 ± 4.7 |
| 'A' | 2 | 648 | 53 ± 3.3 P < 0.02 | 54 ±3.2 P < 0.02 | 59 ± 2.7 P < 0.01 | 54 ± 1.9 P < 0.01 |

The results shown in Table VI above indicate that N-acetyl-para-aminophenyl N'-acetyl-D,L-methionate (Compound A) has a statistically-significant analgesic effect at the 2 millimoles/kg level, which is at least as great as N-acetyl-para-aminophenol (NAPA) judging from the level of the statistical significance reached.

(D)—Investigation of Antipyretic Activity in Rats

Using the conventional procedure for the yeast-induced hyperthermia test, several groups of 10 male Charles River rats were given a subcutaneous injection of dried yeast. Immediately after the injection they were then medicated orally with respectively:

100 mg/kg of N-acetyl-para-aminophenol (NAPA);
90 mg/kg of NAPA + 21.5 mg/kg of Compound A;
80 mg/kg of NAPA + 43.0 mg/kg of Compound A; and
60 mg/kg of NAPA + 86.0 mg/kg of Compound A.

In the mixtures the amount of Compound A, N-acetyl-para-aminophenyl N'-acetyl-D,L-methionate, used was in each case equimolar with the 10%, 20% or 40% reduction in the amount of NAPA, so that all the medications were carried out at a level equivalent to 100 mg/kg of NAPA.

RESULTS

The body temperature of each rat was carefully monitored for 6 hours following oral administration of the NAPA and NAPA/Compound A mixtures, and the results obtained showed that the four treatments had similar antipyretic effects, each starting at about 39.7° C. and all ranging at about 37.8° to 38.0° C. after 1 hour, about 38.2°–38.6° C. after 2 hours, about 38.9°–39.5° C. after 3 hours and about 39.5°–39.6° C. after 4 hours. It can therefore be concluded that the antipyretic effect of Compound A, N-acetyl-para-aminophenyl N'-acetyl-D,L-methionate, is virtually identical upon an equimolar basis of comparison with that of the well-tried analgesic NAPA, N-acetyl-para-aminophenol.

(E)—Investigation of Acute Oral Toxicity in Mice

Charles River (CD-1 COBS) albino mice, 20–22 g in weight, were kept for some days in an air-conditioned animal house and fed with a standard diet (sterile VAR granules). They were fasted overnight before experiment, with water ad libitum. 15 Male mice and 15 female mice were used for each experiment.

N-Acetyl-para-aminophenol (NAPA) and N-acetyl-para-aminophenyl N'-acetyl-D,L-methionate (Compound A) were then administered to the mice, orally, as a suspension (shaken continuously with an electromagnetic agitator) in 5% gum arabic at a volume of 0.02 ml/g, either individually or in variously proportioned mixtures and at different dose levels, as shown in Table VII below.

TABLE VII

| NAPA/Compound A Ratio (where applicable) | N—acetyl-para-aminophenol [NAPA] in mg/kg | + | N—acetyl-para-aminophenol N'—acetyl-D,L-methionate [Compound A] in mg/kg |
|---|---|---|---|
| not applicable [100% NAPA] | 350 | + | 0 |
| | 700 | + | 0 |
| | 1400 | + | 0 |
| 450/100 | 350 | + | 77.8 |
| | 700 | + | 155.6 |
| | 1400 | + | 311.1 |
| 400/200 | 400 | + | 200 |
| | 800 | + | 400 |
| | 1600 | + | 800 |
| 300/400 | 450 | + | 600 |
| | 900 | + | 1200 |
| | 1800 | + | 2400 |
| not applicable [100% Compound A] | 0 | + | 2000 |
| | 0 | + | 4000 |

A control group received only the 5% gum arabic vehicle. The mice were observed for 7 days, their behavioural patterns and mortality being recorded.

Results

The behaviour of the mice treated at the highest dose level of the various mixtures was similar to that observed in the mice medicated with N-acetyl-para-aminophenyl N'-acetyl-D,L-methionate alone at the 4 g/kg dose level and with N-acetyl-para-aminophenol alone at the 1400 mg/kg dose level. The animals developed hypothermia, tremor, tail extension, epistaxis and acrocyanosis, followed by death.

The animals which died at lower dose levels did not however present these symptoms.

The $LD_{50}$'s at 24 hours and 7 days were calculated by the Miller and Tainter method, expressing the $LD_{50}$ for the mixture as the total quantity of N-acetyl-para-aminophenol given to the animal, assuming that all the N-acetyl-para-aminophenol from Compound A is available, and thus on the basis that 100 mg of N-acetyl-para-aminophenyl N'-acetyl-D,L-methionate gives 46.6 mg of N-acetyl-para-aminophenol. The results thus calculated are set out in Table VIII below.

TABLE VIII

| NAPA/Compound A Ratio (where applicable) | $LD_{50}$ expressed in N-acetyl-para-aminophenol (NAPA) mg/kg | | Ratio of "total NAPA" [derived both from NAPA proper and from Compound A] relative to Methionine |
|---|---|---|---|
| | after 24 hours | after 7 days | |
| not applicable [100% NAPA] | 730 ± 65 | 690 ± 65 | ∞ |
| 450/100 | 1000 ± 65 | 800 ± 70 | 10:1 |
| 400/200 | 1040 ± 135 | 930 ± 90 | 5:1 |
| 300/400 | 1730 ± 185 | 1500 ± 115 | 5:2 |
| not applicable [100% Compound A] | ≧4000 | ≧4000 | 0 |

From the results set out in Table VIII above it is readily apparent not only that the $LD_{50}$ of Compound A, N-acetyl-para-aminophenyl N'-acetyl-D,L-methionate, is several times greater than that of the well-tried analgesic NAPA, N-acetyl-para-aminophenol, but furthermore that the presence of even a quite minor proportion of Compound A in mixtures thereof with NAPA brings about a substantial increase in the $LD_{50}$ of such mixtures as compared with NAPA, thus demonstrating the hepatic safety of such compositions.

(F)—Investigation of Acute Oral Toxicity in Rats

The investigation was carried out upon groups of 10 male and 10 female albino rats (Charles River CD-1 COBS) of 80–100 g body weight. The rats were kept for some days in an air-conditioned animal house, and fed with a standard diet and drinking water ad libitum. Before the experiment they were fasted overnight, with water ad libitum. NAPA and Compound A were then administered orally by oesophageal intubation as suspensions (continuously shaken with an electromagnetic agitator) in 1% gum arabic at a volume of 2 ml/100 g body weight, and at dose levels of 1, 2, 4 and 8 g/kg. A control group received orally, under the same experimental conditions, merely 2 ml/100 g of the suspension vehicle. The rats were then kept under observation during seven days, while their behaviour patterns were observed and the mortality recorded As regards behaviour, no alteration was observed in the behavioural patterns of the rats treated with Compound A—but administration of NAPA induced complete prostration and hypothermia in all the rats at levels of 2, 4 and 8 g/kg, half an hour after the administration. Hair erection and continual watering of the eyes appeared two hours after the administration. The first deaths were noticed eight hours after the administration at 8 g/kg dose level, with convulsions of tetanic type, epistaxis, blood tears and acrocyanosis.

As regards mortality, in the case of Compound A no mortality was recorded at any of the different dose levels, as appears from Table IX below. Heavy mortality was however recorded in the case of NAPA, especially at the higher dose levels as appears from Table X below.

TABLE IX

| Compound A | Number and Sex | Acute Toxicity Percentage Mortality | | | | | | |
|---|---|---|---|---|---|---|---|---|
| | | 24 Hours | 48 Hours | 3 Days | 4 Days | 5 Days | 6 Days | 7 Days |
| 8 g/kg | 10 M | 0 | 0 | 0 | 0 | 0 | 0 | 0 |
| | 10 F | 0 | 0 | 0 | 0 | 0 | 0 | 0 |
| | M & F | 0 | 0 | 0 | 0 | 0 | 0 | 0 |
| 4 g/kg | 10 M | 0 | 0 | 0 | 0 | 0 | 0 | 0 |
| | 10 F | 0 | 0 | 0 | 0 | 0 | 0 | 0 |

TABLE IX-continued

| | | Acute Toxicity Percentage Mortality | | | | | | |
|---|---|---|---|---|---|---|---|---|
| Compound A | Number and Sex | 24 Hours | 48 Hours | 3 Days | 4 Days | 5 Days | 6 Days | 7 Days |
| | M & F | 0 | 0 | 0 | 0 | 0 | 0 | 0 |
| | 10 M | 0 | 0 | 0 | 0 | 0 | 0 | 0 |
| 2 g/kg | 10 F | 0 | 0 | 0 | 0 | 0 | 0 | 0 |
| | M & F | 0 | 0 | 0 | 0 | 0 | 0 | 0 |
| | 10 M | 0 | 0 | 0 | 0 | 0 | 0 | 0 |
| 1 g/kg | 10 F | 0 | 0 | 0 | 0 | 0 | 0 | 0 |
| | M & F | 0 | 0 | 0 | 0 | 0 | 0 | 0 |
| | 10 M | 0 | 0 | 0 | 0 | 0 | 0 | 0 |
| CONTROL | 10 F | 0 | 0 | 0 | 0 | 0 | 0 | 0 |
| | M & F | 0 | 0 | 0 | 0 | 0 | 0 | 0 |

TABLE X

| | | Acute Toxicity Percentage Mortality | | | | | | |
|---|---|---|---|---|---|---|---|---|
| NAPA | Number and Sex | 24 Hours | 48 Hours | 3 Days | 4 Days | 5 Days | 6 Days | 7 Days |
| | 10 M | 90 | 100 | 100 | 100 | 100 | 100 | 100 |
| 8 g/kg | 10 F | 100 | 100 | 100 | 100 | 100 | 100 | 100 |
| | M & F | 95 | 100 | 100 | 100 | 100 | 100 | 100 |
| | 10 M | 90 | 90 | 90 | 90 | 90 | 90 | 90 |
| 4 g/kg | 10 F | 70 | 70 | 70 | 70 | 70 | 70 | 70 |
| | M & F | 80 | 80 | 80 | 80 | 80 | 80 | 80 |
| | 10 M | 10 | 10 | 10 | 10 | 10 | 10 | 10 |
| 2 g/kg | 10 F | 0 | 0 | 0 | 0 | 0 | 0 | 0 |
| | M & F | 5 | 5 | 5 | 5 | 5 | 5 | 5 |
| | 10 M | 10 | 10 | 10 | 10 | 10 | 10 | 10 |
| 1 g/kg | 10 F | 0 | 0 | 0 | 0 | 0 | 0 | 0 |
| | M & F | 5 | 5 | 5 | 5 | 5 | 5 | 5 |
| | 10 M | 0 | 0 | 0 | 0 | 0 | 0 | 0 |
| CONTROL | 10 F | 0 | 0 | 0 | 0 | 0 | 0 | 0 |
| | M & F | 0 | 0 | 0 | 0 | 0 | 0 | 0 |

From the results in Tables IX and X above the $LD_{50}s$ at 24 hours and 7 days for both Compound A and NAPA were calculated by the Miller and Tainter method, on logarithmic paper, and were as follows:

Compound A: $LD_{50}$ (24 hrs. and 7 days) > 8 g/kg

NAPA: $LD_{50}$ (24 hrs.) = 3.1 ± 0.5 g/kg  $LD_{50}$ (7 days) = 2.85 ± 0.4 g/kg From this it can be concluded that Compound A when administered orally in 5% gum arabic to the albino COBS rats proved far less toxic than NAPA, and did not induce any mortality at dose levels up to 8 g/kg.

We claim:

1. para-Aminophenyl N-acetylaminothioalkanoate of general formula

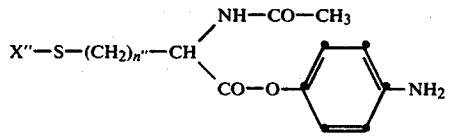

in which n" is 1 or 2, and X" is a hydrogen atom, a blocking group, a methyl group or a grouping of the general formula

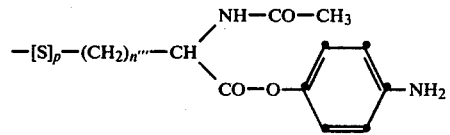

wherein n''' is 1 or 2, and p is zero or 1.

2. para-Nitrophenyl N'-acetylaminothioalkanoate having the general formula

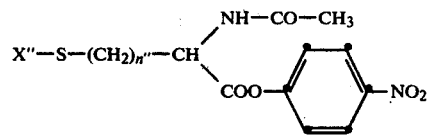

in which n" is 1 or 2, and X" is a hydrogen atom, tetrahydro-2-pyranyl as a blocking group, a methyl group or an ester conforming to the general formula

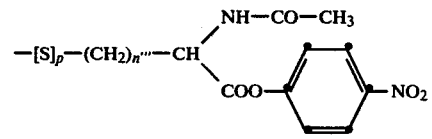

wherein n''' is 1 or 2, and p is zero or 1.

* * * * *